United States Patent [19]

Dougherty et al.

[11] Patent Number: 5,274,148
[45] Date of Patent: Dec. 28, 1993

[54] DIALKY ALKOXY PHENYL SULFONIUM SALT CATIONIC INITIATORS

[75] Inventors: James A. Dougherty, Pequannock, N.J.; James V. Crivello, Clifton Park, N.Y.

[73] Assignee: ISP Investments, Inc., Wilmington, Del.

[21] Appl. No.: 926,426

[22] Filed: Aug. 10, 1992

[51] Int. Cl.$^5$ ............................ C07F 9/90; C07F 9/02
[52] U.S. Cl. .................................. 556/64; 556/7; 556/13; 568/13; 568/15; 568/18; 252/182.17; 252/183.11
[58] Field of Search ................ 556/64, 7, 13; 568/13, 568/15, 18; 252/182.17, 183.11

[56] References Cited

U.S. PATENT DOCUMENTS

| | | | |
|---|---|---|---|
| 4,058,401 | 11/1977 | Crivello | 96/115 R |
| 4,230,814 | 10/1980 | Crivello | 526/333 |
| 4,319,974 | 3/1982 | Crivello | 204/159.11 |
| 4,374,066 | 2/1983 | Crivello et al. | 260/440 |
| 4,882,201 | 11/1989 | Crivello et al. | 427/54.1 |
| 5,159,088 | 10/1992 | Schwalm | 549/3 |

*Primary Examiner*—José G. Dees
*Assistant Examiner*—Porfirio Nazario
*Attorney, Agent, or Firm*—Marilyn J. Maue; Joshua J. Ward

[57] ABSTRACT

This invention relates to $C_{14}$ to $C_{20}$ alkoxy monophenyl sulfonium salt initiators having the formula $$RO-C_6H_4-\overset{\overset{\displaystyle R_1}{|}}{\underset{\underset{\displaystyle R_2}{|}}{S}}{}^+X^-$$

wherein R is $C_{14}$ to $C_{20}$ alkyl; $R_1$ and $R_2$ are each independently $C_4$ to $C_{20}$ alkyl and $X^-$ is a non-basic, nonnucleophilic anion, which initiators are employed in the polymerization of mono- and poly- functional glycidyl ethers, alpha-olefin oxides and vinyl monomers or oligomers.

9 Claims, No Drawings

DIALKY ALKOXY PHENYL SULFONIUM SALT CATIONIC INITIATORS

In one aspect this invention relates to certain cationic initiators which have markedly improved solubility in hydrocarbons and ethers.

In another aspect, the invention relates to a cationic polymerization initiator which is prepared by a simple process and to the use of these certain cationic initiators in the polymerization of alpha-olefins, epoxides and other monomers or oligomers containing long chain hydrocarbon groups.

BACKGROUND OF THE INVENTION

Photoinitiated cationic polymerization has received considerable attention in recent years as way to prepare 100% reactive coatings, inks, and adhesives. Accordingly, various cationic initiators have been developed, many of which are based on sulfonium and iodonium organic salts. However, most iodonium organic salts have been found to be unstable in the presence of highly reactive monomers. Of the sulfonium salts, those found to be useful include the triaryl sulfonium salts described in U.S. Pat. No. 4,374,066, dialkyl phenacyl sulfonium salts described in U.S. Pat. Nos. 4,058,401 and dialkyl hydroxyaryl sulfonium salts described in U.S. Pat. No. 4,230,814. Although useful for initiating the polymerization of a number of cationically polymerizable resins including epoxides, cyclic ethers and vinyl ethers, these highly polar, crystalline initiators are not readily soluble in non-polar solvents. Therefore, they are unsuitable for initiating the polymerization of long chain resins such as long chain alpha-olefin oxides and alkyl vinyl ethers.

Recently, the preparation and use of triphenyl alkoxy sulfonium salt photoinitiators has been described in U.S. Pat. No. 4,882,201. Since it is now determined that hydrocarbon solubility improves with increasing length of an alkoxy chain group, these salts may be more suitable for initiating the cationic polymerizations of non-polar monomers and oligomers; however, increasing the alkyl chain length also increases crystallinity as indicated by a correspondingly increasing melting point. Hence, it is found that patentees' photoinitiators with long alkoxy chains must be heated to relatively high temperatures in order to effect their dissolution; thus, they are unsuitable for formulations involving volatile resins. A further drawback is that, since these initiators are only soluble in hydrocarbon resins at elevated temperatures, they tend to recrystallize out of solution at room temperature. The multicyclic alkaryl sulfonium salts of U.S. Pat. No. 4,319,974 also have been disclosed as cationic initiators; however, these display the same inability to remain in solution and recrystallize at or about room temperature.

Accordingly, it is an object of this invention to provide a cationic initiator having markedly improved solubility in long chain hydrocarbons or hydrocarbon ethers at room temperature.

Another object is to provide a cationic initiator which does not crystallize from a coating formulation at room temperature and which is effectively employed in a polymerization system involving hydrocarbon or volatile resins.

Another object is to provide a process for curing alpha-olefin and glycidyl ether monomers or oligomers under mild conditions which is both economical and convenient.

These and other objects of the invention will become apparent from the following description and disclosure.

THE INVENTION

The present invention is based on the discovery that certain dialkyl monoalkoxy phenyl sulfonium salts are unexpectedly and substantially more soluble in hydrocarbon resins than their corresponding polyphenyl alkoxy analogs and, unlike the latter, do not crystallize from coating formulations at room temperature. The cationic initiators of the present invention are described by the formula

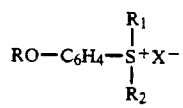

wherein R is $C_{14}$ to $C_{20}$ alkyl; $R_1$ and $R_2$ are each independently $C_4$ to $C_{20}$ alkyl and $X^-$ is a non-basic, nonnucleophilic anion; examples of which include $SbF_6^-$, $AsF_6^-$, $PF_6^-$, $BF_4^-$, $ClO_4^-$, $CF_3SO_3^-$ and the like.

Preferred examples of instant cationic initiators are antimony hexafluoride salts wherein R is a $C_{14}$ to $C_{18}$ alkyl and wherein $R_1$ and $R_2$ are each independently $C_4$ to $C_{12}$ alkyl or mixtures of said initiators.

Examples of these initiators include

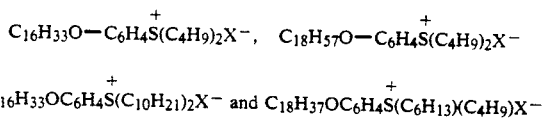

These UV photoinitiators include those which absorb in the mid and far ultraviolet ranges of the spectrum and can have their absorption capability extended by incorporating known photosensitizers as taught in Crivello and Lam, Journal of Polymer Science, 17, 1059 (1979).

The present initiators are employed with monomers or oligomers of mono- or poly- functional glycidyl ethers, alpha-olefin oxides or vinyl compounds in a concentration of from about 0.1 to about 10 wt. %, preferably from about 0.3 to about 5 wt. %.

The cationic photoinitiators of this invention are conveniently prepared in accordance with the following representative reactions

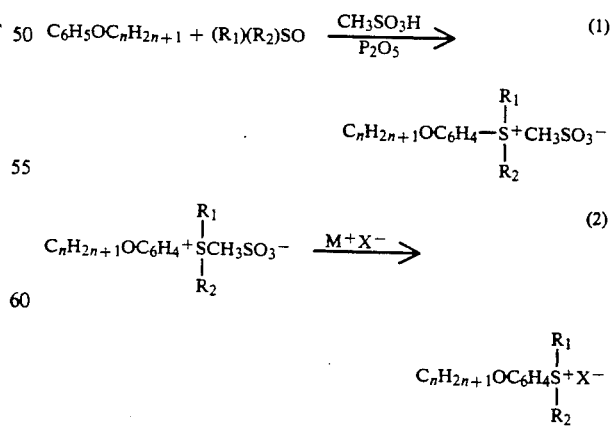

wherein n has a value of from 14 to 20; $R_1$ and $R_2$ are as defined above; $M^+$ is a cation and $X^-$ is a non-basic, nonnucleophilic anion as identified. The above reactions are carried out at a temperature of between about 0° and about 70° C., preferably between about 20° and about 35° C. under atmospheric pressure with constant agitation over a period of from 1 to 24 hours in the presence of a solvent. Suitable solvents, in addition to methane sulfonic acid, include methylene chloride, carbon tetrachloride, and the like.

The sulfonium salt product is then recovered in a substantially pure state by filtration, washing and purified further by recrystallization.

The crystalline cationic photoinitiator can be then dissolved in the monomer or oligomer of choice, coated on a substrate of paper, glass, plastic or metal to a thickness of from about 0.5 to 5 mils, usually from about 0.8 to about 2 mils and then cured.

The coating mixture is cured by exposure to radiation such as supplied by Uv light, ionizing radiation, laser radiation etc. at about room temperature until a tack-free film is obtained.

Suitable monomers or oligomers which are curable with the present initiators include vinyl anisole, styrene, lauryl vinyl ether, cetyl vinyl ether, octadecyl vinyl ether, cyclohexane dimethanol divinyl ether, bisphenol-A diglycidyl ether, cyclohexeneoxide, butyl glycidyl ether, styrene oxide, phenyl glycidyl ether. The mention of these monomers does not mean to imply that other radiation curable monomers or oligomers cannot be similarly cured using the present initiators, but only that these other monomers do not present the difficulties associated with those above. Such other monomers include tri- or tetra- ethylene glycol divinyl ether, hydroxy butyl vinyl ether, tetrahydrofurfuryl vinyl ether, 3,4-epoxycyclohexyl methyl-3',4'-epoxycyclohexane carboxylate. Of course it will be understood that mixtures of the above monomers or oligomers can be employed.

The improved hydrocarbon solubility of the present initiators renders them suitable for preparing uv-curable non-silicone release coatings as described in the copending U.S. patent application by the same inventors entitled RAPIDLY CURABLE VINYL ETHER RELEASE COATINGS. Also, films of the present cured polymers can also be cast in sheets and used in packaging of comestible and other products or applied as protective coatings on various substrates.

Having generally described the invention, reference is now made to the accompanying examples which illustrate preferred embodiments but which are not to be construed as limiting to the scope of the invention as more broadly described above and in the appended claims.

EXAMPLE 1

A 1-liter three necked round bottom flask was charged with 100 grams (0.33 moles) of 1-bromohexadecane, 92.5 grams (0.99 moles) of phenol, 55.2 grams (0.99 moles) of potassium hydroxide, 10 grams of tetra-n-butylammonium bromide, 167 ml of toluene, and 167 ml of water. The flask was fitted with a mechanical stirrer, nitrogen inlet, condenser, thermometer and heating mantle. The reaction mixture was heated to reflux at about 92° C., under a nitrogen purge for 16 hours with constant agitation. After 16 hours, the mixture was cooled and transferred to a separatory funnel where the aqueous layer was removed and the upper toluene layer was washed three times with 200 ml 0.5N NAOH and three times with 200 ml deionized water. The toluene was removed under reduced pressure leaving 102.6 grams (98% yield) of n-hexadecyl phenyl ether. Analysis by gas chromatography showed that the product was 98.3% pure.

A 250 ml three necked flask equipped with a mechanical stirrer and dropping funnel was charged with 12.72 grams (0.04 moles) of n-hexadecyl phenyl ether, 15 grams of methylene chloride, and 20 ml of a 1:10 mixture of $P_2O_5$ dissolved in methanesulfonic acid. A solution of 6.5 grams (0.04 moles) of n-butyl sulfoxide dissolved in 25 grams of methylene chloride was added dropwise with constant stirring while maintaining the reaction temperature below 25° C. After 23 hours, the reaction mixture was poured into 200 ml deionized water and transferred to a separatory funnel where the aqueous layer was removed. The methylene chloride layer was mixed with 200 ml of acetone containing 10.36 grams (0.04 moles) $NaSbF_6$. After 1 hour, the solution was filtered and the acetone was removed under reduced pressure. The crude product was recrystallized from methanol to give 15.9 grams (56.8% yield) of the sulfonium salt (mp=41°-45° C.) having the formula

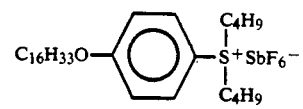

The photoactivity of the above product was confirmed by dissolving 1% by weight in triethylene glycol divinyl ether. A 1 mil film was cast on a glass plate using a #12 Mayer bar and was exposed to UV light. A tack-free film was instantly produced with as little as 60 Mj/CM² UV irradiation.

EXAMPLE 2

Example 1 is repeated except that an equivalent amount of the sodium salts of non-nucleophilic anions $AsF_6^-$, $PF_6^-$, $BF_4^-$, $ClO_4^-$, and $CF_3SO_3^-$ were used in place of $NaSbF_6$. The corresponding photoinitiators were recovered in good yield. Photoactivity was tested by dissolving 1% by weight of each product in 1.5 gm triethylene glycol divinyl ether. The resulting solution was placed in an aluminum weighing pan and exposed to 1000 mJ/cm² UV irradiation. In each case a cross-linked polymer was formed immediately.

EXAMPLE 3

Example 1 is repeated except that an equivalent amount of 1-bromooctadecane is used in place of 1bromohexadecane. The corresponding crude product was recrystallized from methanol to give a 65% yield of the sulfonium salt (mp=57°-60° C.) having the formula

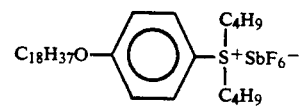

The photoactivity of the above product was confirmed by dissolving 1% by weight in triethylene glycol divinyl ether. A 1 mil film was case on glass using a #12 mayer bar and was exposed to UV light. A tack-free film was instantly produced with as little as 60 mJ/cm² UV irradiation.

EXAMPLE 4

Example 3 is repeated except an equivalent amount of methyl sulfoxide is used in place of N-butyl sulfoxide. The following photoinitiator (mp=76°-82° C.) having the formula

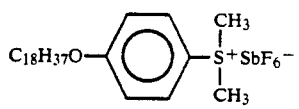

was recovered.

The photoactivity of the above product was confirmed by dissolving 1% by weight in triethylene glycol divinyl ether at 80° C. A 1 mil film was immediately cast on glass using a #12 Mayer bar and was exposed to UV light. A tack-free film was produced instantly with as little as 60 mJ/cm² UV irradiation.

EXAMPLE 5

Example 4 is repeated except that an equivalent amount of decyl sulfoxide is used in place of the methyl sulfoxide. The resulting crude product was a viscous oil which was purified by washing with methanol to give the following photoinitiator

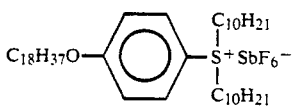

EXAMPLE 6

The solubility of the above sulfonium hexafluoroantimonate salts were compared on an equivalent weight basis to the following previously developed photinitiators:

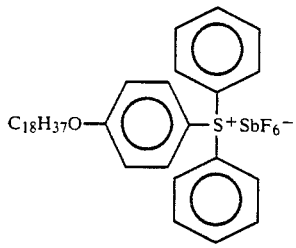

mp = 92-95° C.

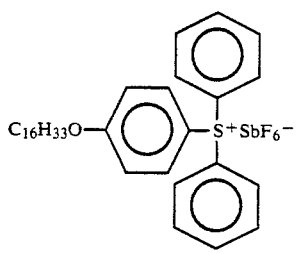

mp = 90-93° C.

A release coating was prepared using the following formulae:

0.38 equivalents dodecyl vinyl ether
0.20 equivalents triethylene glycol divinyl ether
$5.8 \times 10^{-4}$ equivalents photoinitiator Components were blended by warming the mixture to a temperature slightly above the melting point of the initiator in order to advance dissolution of the photoinitiator and then allowed the solution to cool to 25° C. in a water bath. The compositions were observed after 4 hours for any photoinitiator precipitation. The results clearly demonstrate the unexpected and improved solubility of the dialkyl alkoxyphenyl sulfonium salts of this invention.

| PHOTOINITIATOR | SOLUBILITY |
| --- | --- |
| $C_{16}H_{33}O$—⟨phenyl⟩—$S^+SbF_6^-$ with two $C_4H_9$ groups | no crystallization |
| $C_{18}H_{37}O$—⟨phenyl⟩—$S^+SbF_6^-$ with two $C_4H_9$ groups | no crystallization |
| $C_{18}H_{37}O$—⟨phenyl⟩—$S^+SbF_6^-$ with two $CH_3$ groups | recrystallization |
| $C_{18}H_{37}O$—⟨phenyl⟩—$S^+SbF_6^-$ with two $C_{10}H_{21}$ groups | no crystallization |
| $C_{18}H_{37}O$—⟨phenyl⟩—$S^+SbF_6^-$ with two phenyl groups | recrystallization |
| $C_{16}H_{33}O$—⟨phenyl⟩—$S^+SbF_6^-$ with two phenyl groups | recrystallization |

It will be understood that other initiators of this invention can be substituted for those in Examples 1, 2, 3 or 5 to achieve similar results and also that any of the other monomers or oligomers described above can be substituted in these Examples to provide tack-free coatings.

We claim:

1. The sulfonium salt photoinitiator having the formula

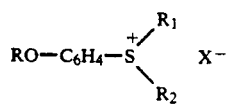

wherein R is alkyl having 16 or 18 carbon atoms; $R_1$ and $R_2$ are each independently alkyl having 4, 6 or 10 carbon atoms and $X^-$ is a non-basic, non-nucleophilic anion.

2. The salt initiator of claim 1 having the formula

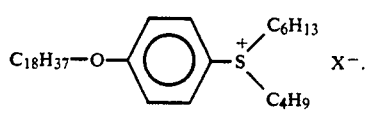

3. The salt initiator of claim 2 having the formula

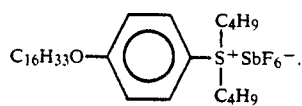

4. The salt initiator of claim 2 having the formula

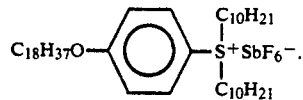

5. The salt initiator of claim 2 having the formula

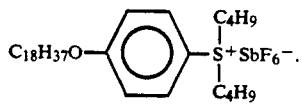

6. The salt initiator of claim 2 having the formula

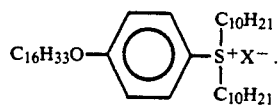

7. A cationically curable composition comprising a cationically polymerizable monomer or oligomer containing between about 0.1 and about 10 wt. % of the salt initiator of claim 2.

8. The composition of claim 7 wherein said monomer or oligomer contains between about 0.3 and about 5 wt. % of said salt initiator.

9. The composition of claim 7 wherein said cationically polymerizable monomer or oligomer is the monomer or oligomer containing a long chain hydrocarbon group and is selected from the group of a vinyl ether, a glycidyl ether and an alpha-olefin oxide.

* * * * *